United States Patent [19]

Sircar

[11] 4,397,854

[45] Aug. 9, 1983

[54] SUBSTITUTED 6-PHENYL-3(2H)-PYRIDAZINONES USEFUL AS CARDIOTONIC AGENTS

[75] Inventor: Ila Sircar, Ann Arbor, Mich.

[73] Assignee: Warner-Lambert Company, Morris Plains, N.J.

[21] Appl. No.: 325,719

[22] Filed: Nov. 30, 1981

Related U.S. Application Data

[63] Continuation-in-part of Ser. No. 263,643, May 14, 1981.

[51] Int. Cl.$^3$ .................... A61K 31/50; C07D 237/04; C07D 237/14
[52] U.S. Cl. ..................................... 424/250; 544/239
[58] Field of Search .......................................... 424/750

[56] References Cited

U.S. PATENT DOCUMENTS 4,107,315  8/1978  Lesher et al. ...................... 544/239

FOREIGN PATENT DOCUMENTS 884859  2/1981  Belgium .
54-19987  8/1979  Japan .
2057438  8/1980  United Kingdom .

OTHER PUBLICATIONS

Jahine et al., Pak. J. Sci. 30, 1–6, (1978).
Kulkarni, *Current Science* 46, 801, (1977).
17446 D/11 Derwent Abstract of Belgian Pat. No. 884,859, also enclosed.
Haginiwa, et al., Yakugaki Zasshi, 98, 67–71, (1978).
McEvoy, et al., J. Med. Chem., 17, 281, (1974).
Abstract of Germ. Pat. No. DT 2435–244.
Abstract of Germ. Pat. No. DT 2445–681.
William Curran et al., J. Med. Chem., 17, 273, (1974).
Luis Pitarch et al., Eur. Med. Chem., Chimica Therapeutica, No. 6, 644, (1974).
Abstract of U.S. Pat. No. 4152–517.
Abstract of Japanese Pat. No. J51043–776.
Abstract of European Pat. EP No. 8391.
Abstract of European Pat. EP No. 10156.

*Primary Examiner*—Mark L. Berch
*Attorney, Agent, or Firm*—Walter Patton

[57] ABSTRACT

Substituted 6-phenyl-3(2H)-pyridazinone compounds are useful as cardiotonic agents.

Said compounds cause a significant increase in myocardial contractility in the anesthetized dog. Said compounds are produced by reacting substituted γ-oxobenzenebutanoic acids with suitably substituted hydrazines to provide 6-phenyl-4,5-dihydro-3(2H)-pyridazinones which are dehydrogenated to the desired product.

The intermediate 6-phenyl-4,5-dihydro-3(2H)-pyridazinones are themselves useful as cardiotonic agents.

5 Claims, No Drawings

SUBSTITUTED 6-PHENYL-3(2H)-PYRIDAZINONES USEFUL AS CARDIOTONIC AGENTS

This is a continuation-in-part application of copending U.S. patent application Ser. No. 263,643, filed May 14, 1981.

BACKGROUND OF THE INVENTION

The present invention relates to the method of use of substituted 6-phenyl-3(2H)-pyridazinones and 6-phenyl-4,5-dihydro-3(2H)-pyridazinones as cardiotonic agents.

SUMMARY OF THE INVENTION

The present invention relates to the method for increasing cardiac contractility in a patient requiring such treatment which comprises administering orally or parenterally in a solid or liquid dosage form to such a patient an effective amount of prior known compounds having the structure:

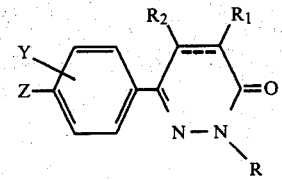

wherein ═══ represents a double or single bond between two carbon atoms; R is hydrogen, lower alkyl, phenylmethyl, dialkylaminoalkyl or hydroxyalkyl; $R_1$ and $R_2$ are independently hydrogen, lower alkyl or phenylmethyl with the proviso that at least one of them is hydrogen. Y and Z are independently hydrogen, halogen, lower alkyl, lower alkoxy, hydroxy, phenoxy, CN, or $NR_3R_4$ wherein $R_3$ is hydrogen or lower alkyl and $R_4$ is hydrogen, lower alkyl or acyl of lower alkyl wherein lower alkyl and lower alkoxy contain one to three carbon atoms; and the pharmaceutically acceptable salts thereof.

The compounds of formula I where R is hydrogen may exist in tautomeric forms, that is, as 6-phenyl-3(2H)-pyridazinones of formula I and/or 6-phenyl-3-pyridazinols of formula IA, illustrated as follows.

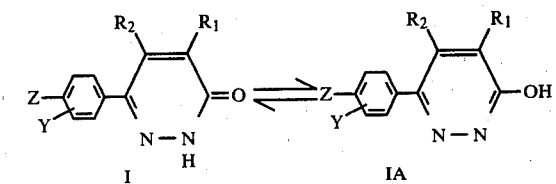

The present invention further relates to the method for increasing cardiac contractility in a patient requiring such treatment which comprises administering orally or parenterally in a solid or liquid dosage form to such patient an effective amount of prior known compounds having the structural formula II

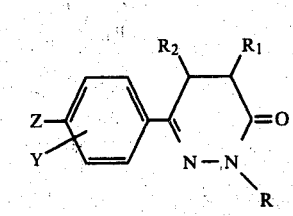

wherein R, $R_1$, $R_2$, Y, and Z are defined as above.

The preferred aspect of the present invention relates to the method for increasing cardiac contractility in a patient requiring such treatment which comprises administering orally or parenterally in a solid or liquid dosage form to such patient an effective amount of prior known compounds having the structural formula III and IV

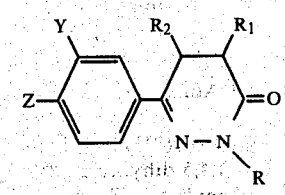

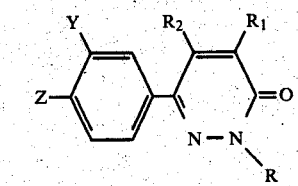

wherein R and $R_2$ are hydrogen or lower alkyl, $R_1$ is hydrogen and Y and Z are independently hydrogen, halogen, lower alkyl, lower alkoxy, hydroxy, phenoxy, CN or $NR_3R_4$ wherein $R_3$ is hydrogen or lower alkyl and $R_4$ is hydrogen, lower alkyl or acyl of lower alkyl wherein lower alkyl and lower alkoxy contain one to three carbon atoms; and the pharmaceutically acceptable salts thereof.

The present invention further relates to a method for increasing cardiac contractility which comprises the administration of a medicament comprising an effective amount of the compound of formula (I) and (II) and a pharmaceutically acceptable carrier.

The process for producing 6-phenyl-3(2H)-pyridazinones comprises reacting substituted ⊖-oxobenzenebutanoic acid with suitably substituted hydrazines to give 6-phenyl-4,5-dihydro-3(2H)-pyridazinones which can be dehydrogenated to the desired product by known dehydrogenation procedures such as bromination-dehydrobromination; by noble metal catalyzed dehydrogenation such as palladium catalyzed dehydrogenation or by oxidation-reduction procedures using m-nitrobenzene sulphonic acid as the reagent according to the standard literature procedure set forth in W. V. Curran and Adma Ross, J. Med. Chem., 17, 273 (1974).

The compounds of formulas (I) and (II) are useful both in the free base form and in the form of acid addition salts; and, both forms are within the scope of the invention. The acid addition salts are a more convenient form for use; and, in practice, use of the salt form amounts to use of the base form. In practicing the invention, it was found convenient to form the sulfate, phosphate, or methanesulfonate. Howver, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate and the like respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The following examples will further illustrate the invention without, however, limiting to thereto.

EXAMPLE 1

6-phenyl and the following substituted 6-phenyl-4,5-dihydro-3(2H)-pyridazinone compounds are prepared according to the standard literature procedure set forth in W. V. Curran and Adma Ross, J. Med. Chem., 17, 273, (1974).

1A. 6-phenyl-4,5-dihydro-3(2H)-pyridazinone
2A. 6-(4-fluorophenyl)-4,5-dihydro-3(2H)-pyridazinone
3A. 6-(4-chlorophenyl)-4,5-dihydro-3(2H)-pyridazinone
4A. 6-(3,4-dichlorophenyl)-4,5-dihydro-3(2H)-pyridazinone
5A. 6-(3,4-dimethoxyphenyl)-4,5-dihydro-3(2H)-pyridazinone
6A. 6-(3,4-dihydroxyphenyl)-4,5-dihydro-3(2H)-pyridazinone
7A. 6-(4-methylphenyl)-4,5-dihydro-3(2H)-pyridazinone
8A. 6-(4-phenoxyphenyl)-4,5-dihydro-3(2H)-pyridazinone
9A. 6-(4-acetamidophenyl)-4,5-dihydro-3(2H)-pyridazinone
10A. 5-methyl-6-(4-acetamidophenyl)-4,5-dihydro-3(2H)-pyridazinone
11A. 6-(4-aminophenyl)-4,5-dihydro-3(2H)-pyridazinone
12A. 4-(1,4,5,6-tetrahydro-6-oxo-3-pyridazinyl)-benzonitrile
13A. 5-methyl-6-phenyl-4,5-dihydro-3(2H)-pyridazinone
14A. 4-methyl-6-phenyl-4,5-dihydro-3(2H)-pyridazinone
15A. 2-methyl-6-phenyl-4,5-dihydro-3(2H)-pyridazinone
16A. 2-benzyl-6-phenyl-4,5-dihydro-3(2H)-pyridazinone
17A. 2,6-diphenyl-4,5-dihydro-3(2H)-pyridazinone
18A. 2-[2-(hydroxy)ethyl]-6-phenyl-4,5-dihydro-3(2H)-pyridazinone
19A. 2-[2-(dimethylamino)ethyl]-6-phenyl-4,5-dihydro-3(2H)-pyridazinone

EXAMPLE 2

The dihydro-3(2H)-pyridazinone compounds set forth in Example 1 are dehydrogenated to the corresponding 3(2H)-pyridazinone compounds by the bromination-dehydrobromination procedure set forth in L. Pitarch, R. Coronas and J. Mallol, Eur. J. Med. Chem., Clinica Therapeutica, 9, 644, (1974).

1. 6-phenyl-3(2H)-pyridazinone
2. 6-(4-fluorophenyl)-3(2H)-pyridazinone
3. 6-(4-chlorophenyl)-3(2H)-pyridazinone
4. 6-(3,4-dichlorophenyl)-3(2H)-pyridazinone
5. 6-(3,4-dimethoxyphenyl)-3(2H)-pyridazinone
6. 6-(3,4-dihydroxyphenyl)-3(2H)-pyridazinone
7. 6-(4-methylphenyl)-3(2H)-pyridazinone
8. 6-(4-phenoxyphenyl)-3(2H)-pyridazinone
9. 6-(4-acetamidophenyl)-3(2H)-pyridazinone
10. 5-methyl-6-(4-acetamidophenyl)-3(2H)-pyridazinone
11. 6-(4-aminophenyl)-3(2H)-pyridazinone
12. 4-(1,6-dihydro-6-oxo-3-pyridazinyl)benzonitrile
13. 5-methyl-6-phenyl-3(2H)-pyridazinone
14. 4-methyl-6-phenyl-3(2H)-pyridazinone
15. 2-methyl-6-phenyl-3(2H)-pyridazinone
16. 2-benzyl-6-phenyl-3(2H)-pyridazinone
17. 2,6-diphenyl-3(2H)-pyridazinone
18. 2-[2-(hydroxy)ethyl]-6-phenyl-3(2H)-pyridazinone
19. 2-[2-(dimethylamino)ethyl]-6-phenyl-3(2H)-pyridazinone
20. 4-benzyl-6-phenyl-3(2H)-pyridazinone was synthesized according to the literature procedure set forth in A. M. Kaddah and A. M. Khalil, Indian J. of Chem., 15B, 1025 (1977).

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test for in vivo Myocardial Inotropic Activity in Anesthetized Dog

This screen consists of determining the effects of increasing intravenous doses of compound on myocardial contractility (dp/dT max of left ventricular blood pressure), heart rate and aortic blood pressure of the pentobarbital-anesthetized dog.

Methods

Adult mongrel dogs of either sex are anethetized with pentobarbital, 35 mg/kg, IV, and are subsequently maintained under anesthesia with a continuous infusion of pentobarbital, 3.5 mg/kg/hr. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip recorder. Heart rate, using a biotachometer triggered from the R wave of the ECG, and the first derivative of left ventricular blood pressure (dp/dT), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOh (0.1 or 0.1 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.1 to 1.0 mg/kg/min cause dose related significant increases in cardiac contractility with only low or minimal changes in heart rate and blood pressure.

Test Results of Substituted 6-Phenyl-3(2H)—pyridazinones
Using Anesthetized Dog Procedure
% Change

| Compound Number | Dose mg/kg | Myocardial Contractility | Heart Rate | Blood Pressure |
|---|---|---|---|---|
| 1 | 0.1 | 9.2 | −4 | −2.2 |
|   | 0.31 | 21.7 | +7.5 | +2.2 |
|   | 1.0 | 50.5 | +18.5 | +9.6 |
|   | 3.1 |   |   |   |
| 2 | 0.1 | 20 | 13 | 2.5 |
|   | 0.31 | 0 | 14 | −6.5 |
|   | 1.0 | 48 | 29 | −10.0 |
|   | 3.1 | 50 | 47 | −78.5 |
| 4 | 0.1 | 20 | 0 | 0 |
|   | 0.31 | 76 | 5.1 | −1.7 |
|   | 1.0 | 150 | 15.3 | −2.6 |
|   | 3.1 |   |   |   |
| 5 | 0.1 | 46 | +14.6 | +4.5 |
|   | 0.31 | 112 | +28.8 | −4.6 |
|   | 1.0 | 247 | +59.2 | −10.9 |
|   | 3.1 | 238 | +42.7 | −40.7 |
| 6 | 0.1 | 7 | 5.2 | — |
|   | 0.31 | 28 | 16.2 | — |
|   | 1.0 | 46 | 36.4 | — |
|   | 3.1 | 81 | 51.2 | −8.5 |
| 9 | 0.01 | 26 | 4 | −1 |
|   | 0.03 | 54 | 9 | −1.5 |
|   | 0.1 | 81 | 17 | −5.5 |
|   | 0.3 | 78 | 18 | −13.5 |
| 13 | 0.1 | 7 | +3 | +1 |
|   | 0.31 | 11 | +4 | +2 |
|   | 1.0 | 28 | +7 | +2 |
|   | 3.1 | 55 | +13 | +0 |
| 16 | 0.1 | −1 | −3 | 1.5 |
|   | 0.31 | −3 | 5 | 2.0 |
|   | 1.0 | 24 | 12 | 3.0 |
|   | 3.1 | 59 | 20 | 4.5 |
| 20 | 0.1 | 9 | 0 | 1.5 |
| as HCl | 0.31 | 14 | 3 | 3.5 |
| salt | 1.0 | 29 | 2 | 4.0 |
|   | 3.1 | 49 | 11 | 5.5 |

Test Results of 6-Phenyl-4,5-dihydro-3(2H)—pyridazinones
Using Anesthetized Dog Procedure
% Change

| Compound Number | Dose mg/kg | Myocardial Contractility | Heart Rate | Blood Pressure |
|---|---|---|---|---|
| 1A | 0.1 | 9 | 1 | +1.5 |
|   | 0.31 | 19 | −1 | +1.5 |
|   | 1.0 | 26 | −1 | −1.5 |
|   | 3.1 | 68 | 2 | −0.5 |
| 2A | 0.1 | 13 | 0 | −1 |
|   | 0.31 | 32 | 7 | −3 |
|   | 1.0 | 57 | 7 | −3.5 |
|   | 3.1 |   |   |   |
| 3A | 0.1 | 8 | 0 | −2 |
|   | 0.31 | 25 | 2 | 0 |
|   | 1.0 | 54 | 3 | 0 |
| 4A | 0.1 | 20 | 6 | 0.5 |
|   | 0.31 | 51 | 15 | −4.0 |
| 5A | 0.1 | −6 | −3 | −0.5 |
|   | 0.31 | 13 | 4 | −1.5 |
|   | 1.0 | 100 | 22 | −20.5 |
|   | 3.1 | 163 | 24 | −28.0 |
| 9A | 0.01 | 46 | 5 | −2 |

-continued
Test Results of 6-Phenyl-4,5-dihydro-3(2H)—pyridazinones
Using Anesthetized Dog Procedure
% Change

| Compound Number | Dose mg/kg | Myocardial Contractility | Heart Rate | Blood Pressure |
|---|---|---|---|---|
|   | 0.03 | 94 | 28 | −14 |
|   | 0.1 | 130 | 44 | −16.5 |
|   | 0.3 | 120 | 54 | −26.5 |
|   | 1.0 | 89 | 51 | −36.5 |
| 10A | 0.1 | 16 | 2 | 0.5 |
|   | 0.31 | 45 | 8 | −1.5 |
|   | 1.0 | 103 | 15 | −6.5 |

The actual determination of the numerical cardiotonic data definitive for any other particular compound of the invention is readily obtained according to the above-described standard test procedure by those skilled in pharmacological test procedures, without any need for any extensive experimentation.

The present invention includes within its scope a cardiotonic composition for increasing cardiac contractility, said composition comprising a pharmaceutically acceptable carrier and, as the active component thereof, a cardiotonic compound of the present invention or pharmaceutically acceptable acid addition salt thereof. The invention also includes within its scope and method for increasing cardiac contractility in a patient requiring such treatment which comprises administering to such patient an effective amount of a compound of the present invention or pharmaceutically acceptable acid addition salt thereof. In clinical practice the said compounds of the present invention will normally be administered orally or parenterally in a wide variety of dosage forms.

Solid compositions for oral administration include compressed tablets, pills, powders, and granules. In such solid compositions, at least one of the active compounds is admixed with at least one inert diluent such as starch, calcium carbonate, sucrose, or lactose. These compositions may also contain additional substances other than inert dilutents, e.g., lubricating agents such as magnesium stearate, talc, and the like.

Liquid compositions for oral administration include pharmaceutically acceptable emulsions, solutions, suspensions, syrups, and elixirs containing inert diluents commonly used in the art, such as water or liquid paraffin. Besides inert diluents such compositions may also contain adjuvants, such as wetting and suspending agents, and sweetening, flavoring, perfuming, and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation, or by heating. They may also be manufactured in the form of sterile solid compositions which can be dissolved in sterile water or some sterile injectable medium immediately before use.

The percentage of active component in the said composition and method for increasing cardiac contractility may be varied so that a suitable dosage is obtained. The dosage administered to a particular patient is variable, depending upon the clinician's judgment using as the criteria: The route of administration, the duration of treatment, the size and condition of the patient, the potency of the active component, and the patient's response thereto. An effective dosage amount of active component can thus best be determined by the clinician considering all criteria and utilizing his best judgment on the patient's behalf. However, it is recommended that a useful intravenous dose is between 0.001 and 1 mg/kg. A preferred intravenous dose is 0.01 to 1.0 mg/kg with a still further preferred dose of 0.03 mg/kg. A recommended useful oral dose is 0.01 to 31 mg/kg. A preferred oral dose is 0.1 to 10 mg/kg with a still further preferred dose of 1.0 mg/kg.

What is claimed is:

1. The method for increasing cardiac contractility in a patient requiring such treatment which comprises administering orally or parenterally in a solid or liquid dosage form in a pharmaceutically acceptable carrier to such patient an effective amount of a compound having the structural formula

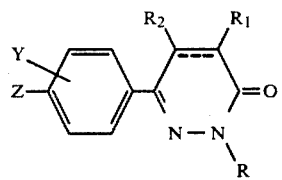

wherein ━━━ represents a double or single bond between two carbon atoms; R is hydrogen, lower alkyl, dialkylaminoalkyl or hydroxyalkyl; $R_1$ and $R_2$ are independently hydrogen, lower alkyl or phenylmethyl with the proviso that at least one of them is hydrogen; Y and Z are independently hydrogen, halogen, lower alkyl, lower alkoxy, hydroxy, phenoxy, CN or $NR_3R_4$ wherein $R_3$ is hydrogen or lower alkyl and $R_4$ is hydrogen, lower alkyl or

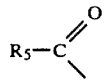

wherein $R_5$ is hydrogen or alkyl containing one or two carbon atoms; wherein lower alkyl and lower alkoxy contain one to three carbon atoms; and the pharmaceutically acceptable salts thereof.

2. The method according to claim 1 wherein said compound has the structure:

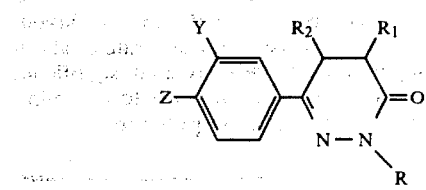

wherein R and $R_2$ are hydrogen or lower alkyl, $R_1$ is hydrogen and Y and Z are as defined in claim 1 and the pharmaceutically acceptable salts thereof.

3. The method according to claim 1 wherein said compound has the structure:

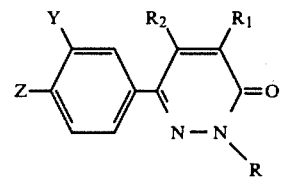

wherein R, $R_1$, $R_2$, Y and Z are as defined in claim 2.

4. The method according to claim 2 wherein said compound is:
   a. 6-phenyl-4,5-dihydro-3(2H)-pyridazinone
   b. 6-(3,4-dichlorophenyl)-4,5-dihydro-3(2H)-pyridazinone
   c. 6-(3,4-dimethoxyphenyl)-4,5-dihydro-3(2H)-pyridazinone
   d. 6-(3,4-dihydroxyphenyl)-4,5-dihydro-3(2H)-pyridazinone
   e. 6-(4-acetamidophenyl)-4,5-dihydro-3(2H)-pyridazinone
   f. 5-methyl-6-(4-acetamidophenyl)-4,5-dihydro-3(2H)-pyridazinone
   g. 2-methyl-6-phenyl-4,5-dihydro-3(2H)-pyridazinone 5. The method according to claim 3 wherein said compound is:
   a. 6-phenyl-3(2H)-pyridazinone
   b. 6-(3,4-dichlorophenyl)-3(2H)-pyridazinone
   c. 6-(3,4-dimethoxyphenyl)-3(2H)-pyridazinone
   d. 6-(3,4-dihydroxyphenyl)-3(2H)-pyridazinone
   e. 6-(4-acetamidophenyl)-3(2H)-pyridazinone
   f. 5-methyl-6-(4-acetamidophenyl)-3(2H)-pyridazinone
   g. 2-methyl-6-phenyl-3(2H)-pyridazinone

* * * * *